(12) United States Patent
Pagliaro et al.

(10) Patent No.: US 7,947,622 B2
(45) Date of Patent: May 24, 2011

(54) AEROBIC CATALYSTS FOR ALCOHOL OXIDATION IN ORGANIC SOLVENTS AND IN SUPERCRITICAL CARBON DIOXIDE, PROCESS FOR THE PRODUCTION THEREOF, AND THEIR USE IN OXIDATIVE CONVERSIONS

(75) Inventors: Mario Pagliaro, Palermo (IT); Rosaria Ciriminna, Palermo (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 1000 days.

(21) Appl. No.: 10/577,367

(22) PCT Filed: Oct. 28, 2004

(86) PCT No.: PCT/IB2004/052230
§ 371 (c)(1),
(2), (4) Date: Mar. 22, 2007

(87) PCT Pub. No.: WO2005/042155
PCT Pub. Date: May 12, 2005

(65) Prior Publication Data
US 2007/0191566 A1     Aug. 16, 2007

(30) Foreign Application Priority Data
Oct. 29, 2003  (IT) ............................. RM2003A0502

(51) Int. Cl.
*B01J 31/12*     (2006.01)
(52) U.S. Cl. ......... 502/164; 502/155; 524/714; 524/785
(58) Field of Classification Search .................. 524/714, 524/785; 502/155, 164
See application file for complete search history.

(56) References Cited

U.S. PATENT DOCUMENTS
6,284,696 B1 * 9/2001 Koya et al. ..................... 502/64

FOREIGN PATENT DOCUMENTS
WO         2005/042155 A3    12/2005

OTHER PUBLICATIONS

"The Effects of Material Properties on the Activity of Sol-Gel Entrapped Perruthenate under Supercritical Conditions", Ciriminna et al. Adv. Synth. Catal. 2003 345, 1261-1267.*
"New recyclable catalysts for aerobic alcohols oxidation: sol-gel ormosils doped with TPAP", Pagliaro et al. Tetrahedron Latters 42 (2001) 4511-4514.*
Pagliaro et al. "New recyclable catalysts for aerobic alcohols oxidation: Sol-gel ormosils doped with TPAP" Tetrahedron Letters, vol. 42, No. 27, pp. 4511-4514 (2001) XP004245731.
Bleloch et al. "Modified mesoporous silicate MCM-41 materials: Immobilised perruthenate—A new highly active heterogenous oxidation catalyst for clean organic synthesis using molecular oxygen" Chem. Commun., pp. 1907-1908 (1999) XP002319966.
Markó et al. "Efficient, aerobic, ruthenium-catalyzed oxidation of alcohols into aldehydes and ketones" J. Am. Chem. Soc., vol. 119, No. 51, pp. 12661-12662 (1997) XP002319967.
Steele et al. "Noble metal catalysed aerial oxidation of alcohols to aldehydes in supercritical carbon dioxide" Catalysis Letters, No. 73, No. 1, pp. 9-13 (2001) XP002319968.
Ciriminna et al. "Tailoring the catalytic performance of sol-gel-encapsulated tetra-n-propylammonium perruthenate (TPAP) in aerobic oxidation of alcohols" Chem. Eur. J., vol. 9, No. 20, pp. 5067-5073 (2003) XP00230336.
Ciriminna et al., "The effect of material properties on the activity of sol-gel entrapped perruthenate under supercritical conditions" Adv. Synth. Catal., vo. 345, pp. 1261-1267 (2003) XP002330337.
International Search Report for PCT/IB2004/052230, two pages, 2005.
International Preliminary Report on Patentability for PCT/IB2004/052230, six pages, 2005.
Ciriminna et al. "Fluorinated silica gels doped with TPAP as effective aerobic oxidation catalysts in dense phase carbon dioxide" Adv. Synth. Catal. 346:231-236 (2004).
Fidalgo et al. "The grounds for the activity of TPAP in oxidation catalysis in supercritical carbon dioxide when confined in hybrid fluorinated silica matrices" Physical Chemistry Chemical Physics 10:2026-2032 (2008).

* cited by examiner

*Primary Examiner* — Margaret G Moore
(74) *Attorney, Agent, or Firm* — Nixon & Vanderhye P.C.

(57) ABSTRACT

Nanohybrid sol-gel materials, based on silica organically modified (ormosil) and doped with the ruthenium species tetra-n-propylammonium perruthenate (TPAP) are highly efficient catalysts for the selective oxidation of alcohols to carbonyls with oxygen at low pressure, in organic solvents as well as in carbon dioxide in supercritical state. Novel, highly active and stable materials are the fluorinated ormosils. Optimal conditions for the preparation and use thereof in liquid-phase as well as in supercritical $CO_2$ were set by studying the structure-activity relationships of the materials, with particular reference to the surface hydrophobic/hydrophilic properties and to the textural ones.

22 Claims, 2 Drawing Sheets

Aerobic benzyl alcohol oxidation to benzaldehyde in $scCO_2$ on TPAP trapped in C3-F-10 10% propyl-fluorinated silicium oxide matrices (rounded points) and 50% methylated TPAP-Me2 (square points)

AEROBIC CATALYSTS FOR ALCOHOL OXIDATION IN ORGANIC SOLVENTS AND IN SUPERCRITICAL CARBON DIOXIDE, PROCESS FOR THE PRODUCTION THEREOF, AND THEIR USE IN OXIDATIVE CONVERSIONS

This application is the U.S. national phase under 35 U.S.C. 371 of Int'l Patent Appn. No. PCT/IB2004/052230, filed 28 Oct. 2004 which designated the U.S. and claims priority benefit of IT RM2003A000502, filed 29 Oct. 2003; the entire contents of each of which are hereby incorporated by reference.

The present invention refers to nanohybrid sol-gel materials, based on silica organically modified and doped with the ruthenium species tetra-n-propylammonium perruthenate (TPAP), to the preparation and use thereof as highly efficient catalysts for the selective oxidation of alcohols to carbonyls with oxygen at low pressure, in organic solvents as well as in carbon dioxide in supercritical state.

These materials are prepared via the sol-gel process, and their catalytic performances can be optimized by modifying the conditions of their synthesis by hydrolytic co-polycondensation of the silica alcoxides in the presence of TPAP. Thus, there are obtained aerobic heterogeneous catalysts significantly more active than the unsupported perruthenate, leach-proof and recyclable.

The present invention provides ormosil catalytic materials even more active than the abovecited materials. Moreover, the use of ormosils in the catalytic reaction of selective oxidation of alcohols is made more effective by the use of carbon dioxide, dense or in supercritical state ($scCO_2$) as oxidation reaction solvent.

A study of the structure-activity relationships is reported, with particular reference to the surface hydrophobic/hydrophilic properties and to the textural ones, obtaining information on the chemical behavior of sol-gel catalytic materials in aerobic oxidation catalysis. These materials are of relevant industrial interest, considering both the applicative importance of solid catalysts for the aerobic oxidation of alcohols and the use of carbon dioxide in supercritical state as reaction medium.

Report on the State of the Art

The selective oxidation of alcohols to carbonyls plays a central role in the synthetic organic chemistry and in the fine chemicals industry, often constituting a key passage for the preparation of important syntheses or for the direct production of important synthons and products of the fine chemicals industry such as fragrances, drugs, vitamins and hormones.

Owing to ever more stringent environmental regulations, the traditional alcohol oxidation processes, used to produce carbonyls, based on the stoichiometric conversion of alcohols to volatile organic compounds (VOCs,) with toxic and hazardous salts of Chromium(VI) or of manganese(IV) or with dimethylsulfoxide (DMSO) have to be replaced by novel eco-efficient catalytic processes utilizing clean and highly atom-efficient oxidants such as hydrogen peroxide ($H_2O_2$) or, better, directly oxygen ($O_2$).

Therefore, in the last 5 years a considerable number of novel mild and highly selective aerobic processes have been discovered, in which very high levels of selective activity are attained mainly by using Ru, Pd, and Cu catalytic species; and in some cases eliminating even the use of the volatile solvents in which these oxidative conversions are traditionally carried out (a feature shared also by a catalyst of W with $H_2O_2$ as primary oxidant).

For all these homogeneous catalytic processes, an efficient catalyst heterogenization method would be highly desirable in order to allow catalyst recycling (and a mere work-up of the product mixture) as well as applications to continuous processes that are those required by industry. Several efforts are currently aimed at the heterogenization of catalytic species soluble in solid materials in which the organometallic part acts as active site and the solid provides the medium for recovering and recycling the active species.

However, for these catalysts the industrial requirements are strict: they should be highly selective (given the number of different oxidizable groups in the molecules of the fine chemicals industry) and stable to a prolonged use. Moreover, they should also be versatile, i.e., applicable to the conversion of a vast number of alcohol substrates of different chemical structure.

In particular, solid catalyst stability is a requirement particularly difficult to attain, since several supported molecules are often labile in oxidizing environments and easily leached in the homogeneous phase, as in the case, relevant under this aspect, of polymer resin (PSP)-supported tetra-n-propylammonium perruthenate (TPAP), a solid catalyst for the aerobic oxidation of alcohols initially declared to be heterogeneous, yet eventually declared useless by the same Authors as being 'unstable and impossible to recycle'. (A. Bleloch, B. F. G. Johnson, S. V. Ley, A. J. Price, D, S, Shephard, A. W. Thomas, *Chem. Commun.*, 1999, 1907).

Moreover, the replacement of the volatile organic solvents used as reaction media (Scheme 1) would be highly desirable, because, as recently highlighted by some researchers in the pharmaceutical industry, "solvents, despite current low prices, in addition to their impacts through use and final disposal, have a considerable life cycle impact and their broader total costs are not cheap".

It has now surprisingly been found, according to the present invention, that carbon dioxide in supercritical state ($scCO_2$) is a highly efficient alternative reaction medium.

First of all, heterogeneous catalytic conversions, which are of primary industrial importance, can be efficiently carried out in $scCO_2$ using small high-throughput reactors in continuous processes where the $CO_2$ is recycled while the substrates are converted, and at the end of the reaction carbon dioxide is completely removed from the products (thanks to its high volatility) resulting in an overall "solvent-free" reaction.

On the other hand, the sol-gel technology for the preparation of reactive materials is increasingly being used for the preparation of highly efficient heterogeneous catalysts, as it allows the encapsulation of virtually any chemical species in the vast internal porosity of porous oxides in which the active molecules are confined and protected in nanoporous cavities where they are accessible to external reactants.

In general, the process is simple and highly reproducible, consisting in the hydrolysis and polycondensation at room temperature of specific precursors (a sol generally—yet not exclusively—consisting of metal alkoxides) carried out in the presence of an alcohol solution of one or more active dopant species; particularly advantageous is the fact that by varying the initial sol composition and the condensation conditions, the structural properties—and therefore the reactivity—of the materials resulting from the process can be controlled and adapted to meet the requirements of specific applications such as chemical catalysis, where the hydrophobic/hydrophilic nature of the catalyst is often crucial; accordingly, e.g., excellent results have recently been proved in the case of liquid-phase esterifications and catalytic oxidations mediated by organically modified silicas (ormosils) whose surface hydrophile/lipophile balance (HLB) proved its deep influence on the activity of the encapsulated molecules.

SUMMARY OF THE INVENTION

According to a first aspect, object of the present invention is a process for the production of nanohybrid sol-gel catalysts for the heterogeneous aerobic catalysis containing tetra-n-propylammonium perruthenate (TPAP) entrapped in the matrix, obtained via a sol-gel process by hydrolysis and co-polymerization of organosilanes and of siloxanes in the presence of said tetra-n-propylammonium perruthenate (TPAP), water and an organic cosolvent, characterized in that said co-polymerization is carried out with a precursor fluorinated organosilane and a non-fluorinated siloxane monomer.

Moreover, it has surprisingly been found in the employment of nanohybrid sol-gel catalytic materials based on silica modified and doped with perruthenate, for the catalysis of aerobic oxidation of alcohols, that $CO_2$ in supercritical state is a reaction solvent of excellent efficiency.

Hence, a second aspect of the invention is a process for the selective heterogeneous aerobic catalytic oxidation of alcohols to carbonyls in a solvent, wherein, as catalyst, it is employed a nanohybrid sol-gel material based on silica organically modified (ormosil) and doped with the ruthenium species tetra-n-propylammonium perruthenate (TPAP), as solvent in the catalytic oxidation reaction it is employed carbon dioxide in supercritical state, and, as primary oxidant, it is employed oxygen, even at a pressure proximal to the atmospheric one.

According to a third aspect of the present invention, there were produced nanohybrid sol-gel catalyst products of superior activity and stability for the heterogeneous aerobic catalysis with tetra-n-propylammonium perruthenate (TPAP) entrapped in the matrix, obtained via a sol-gel process by hydrolysis and co-polymerization of organosilanes and of silanes in the presence of said tetra-n-propylammonium perruthenate (TPAP), water and methanol as organic cosolvent, wherein the ($Si:MeOH:H_2O$) molar ratio among the total silica (organosilane+silane), the amount of cosolvent (MeOH), and the amount of water ($H_2O$), is selected so as to utilize elevated stoichiometric values, both of water and of cosolvent, in particular of 1:8:4, so that the resulting hydrophobic matrices constituting said catalysts exhibit particular reactivity.

The ormosil catalysts of the present invention are versatile and highly stable and selective, can be (re)used for the rapid conversion of various alcohol substrates utilizing as primary oxidant oxygen at room temperature, both in organic solvents (Scheme 1) and in $scCO_2$ (Scheme 2).

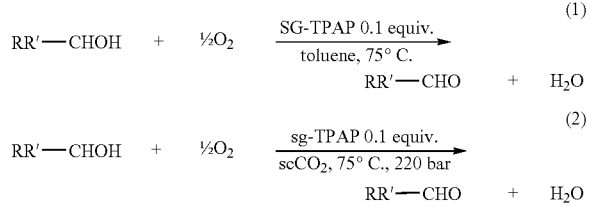

R = Alkyl

The problem underlying the invention is to develop perruthenate-based solid catalysts of aerobic oxidations that, considering the commercial and synthetic relevance of the oxidative dehydrogenations of alcohols and the advantages of the applications of sol-gel materials to catalysis, are deemed leading to practical applications of the invention, useful both industrially and at laboratory level.

For this purpose, according to the first aspect of the present invention it is provided a process for the production of a fluorinated ormosil for the heterogeneous aerobic catalysis exhibiting catalytic performances improved with regard to activity and stability, wherein in the hydrolysis and sol-gel co-polycondensation process there are utilized: as precursor of fluorinated metal alcoxides, a fluorinated organosilane, and, as silane, an organosilane monomer.

Moreover, according to the third aspect of the invention it has been found that the activity and the stability of the TPAP-containing catalyst are generally improved when the matrix in which the perruthenate is dissolved is hydrophobic. For this purpose, it was found that optimal condition to attain such a result is that in the preparation of the ormosil the ($Si:MeOH:H_2O$) molar ratio among the total silica (Si) (organosilane+silane), the amount of cosolvent (MeOH) and the amount of water ($H_2O$), is selected so as to range from 1:4:4 to 1:8:8, preferably of 1:8:4, so that the matrices of said catalysts are hydrophobic.

The catalysts of the present invention, gels of silica organically modified with fluorinated organosilans and doped with TPAP, are significantly more active than the non-fluorinated ones, both in toluene and in $scCO_2$. Their preparation is simple and reproducible, consisting of a sol-gel polymerization process that allows to optimize the catalytic performances of the materials by modifying the surface polarity properties and the textural properties to yield catalysts that are up to 6 times more active than unsupported perruthenate.

According to the invention, the catalysts exhibiting best performances require a high degree of cavity surface hydrophobicity, as well as elevated amounts of water and of cosolvent in the sol-gel polycondensation.

*Heterogeneous* catalytic conversions in "supercritical" carbon dioxide ($scCO_2$) (it should be noted that a critical point is definable for a single-component fluid only, and that in heterogeneous catalysis the term "supercritical" refers to a multicomponent dense, yet single-phase in the reaction) are carried out on an industrial scale by virtue of various practical advantages.

Aside from replacing the volatile organic solvents (VOCs) traditionally used as reaction media with an environmentally benign solvent, the excellent miscibility of the dense phase of $CO_2$ with organic substances and reactants, such as $O_2$ and $H_2$, along with the ultra low viscosity and superior mass transport properties (absence of a gas-liquid phase boundary) allows to carry out high-efficiency continuous heterogeneous processes using small, high-throughput reactors where the $CO_2$ is recycled and eventually completely removed from the products and from the catalyst merely by reducing the pressure, resulting in a closed circuit system or in a "solvent-free" reaction (see, e.g., (a) N. J. Meehan, A. J. Sandee, J. N. H. Reek, P. C. J. Kamer, P. W. N. M. van Leeuwen, M. Poliakoff, *Chem. Commun.* 2000, 1497; (b) M. G. Hitzler, M. Poliakoff, *Chem. Commun.* 1997, 1667).

Oxidations heterogeneously catalyzed in $scCO_2$ are particularly attractive, and yet, as explained by W. Leitner (*Appl. Organom. Chem.* 2000, 14, 809) "largely unexplored"; an efficient aerobic oxidation process of, e.g., an alcohol, would totally eliminate the need of potentially polluting organic solvents and of stoichiometric chrome, manganese, oxides or DMSO used in current industrial conversions. Above all, no costly purification step would be required since high-purity carbonyl reaction products would be obtained, meeting a fundamental requirement for compounds that are widely used as precursors of drugs, vitamins, fragrances and other valuable fine chemicals. Lastly, also safety hazards would be reduced thanks to the complete lack of flammability of $CO_2$.

Few publications relate to the selective dehydrogenation of alcohols in carbon dioxide, all referring to coal-supported noble metals, Pt (R. Gläser, R. Jos, J. Willardt, *Topics in Catal.* 2003, 22, 31 and Steele, J. Zhu, S. C. E. Tsang, *Catalysis Lett.* 2001, 73 (1), 9) or Pd (G. Jenzer, D. M. Sueur, T. Mallat, A. Baiker, *Chem. Commun.* 2000, 2247).

In all cases, the reported catalytic activity in $scCO_2$ is lower than that in liquid-phase, yet dense-phase $CO_2$ suppresses any alcohol overoxidation and considerably improves the stability of the catalyst, which produces carbonyls in high yields and with excellent selectivity. Unfailingly, the increase in hydrophobicity of the catalyst support improves the activity of the material, i.e. the Teflon-coated carbon>carbon (as described by Steele et al.) and the carbon>coal as described in Glaser et al.

Under the conditions of pressure and temperature employed in such heterogeneous catalyses, $CO_2$ has a low dielectric constant, yet it is a markedly fluorophilic species capable of dissolving fluorinated materials in important chemical applications.

The present invention proves that the sol-gel process is a versatile and reproducible method for preparing fluorinated hydrophobic (water-repellent) ormosil catalytic materials.

According to an aspect of the present invention, fluorinated silica gels (FSGs) doped with $[NPr_4]^+[RuO_4]^-$ are efficient catalysts for the dehydrogenation of alcohols in $scCO_2$ with $O_2$ at low pressure (Scheme 3).

Scheme 3

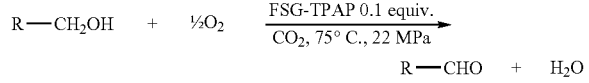

R—CHO + $H_2O$

The scheme reported above is merely exemplary, and not intended as limiting in any way the field of the present invention. The general idea consists in the fact that the catalyst is entrapped in a fluorinated matrix of porous sol-gel and the alcohol substrate and the $O_2$ are dissolved in dense-phase carbon monoxide that, into contact with the powder hydrophobic sol-gel material, drives the reactants within the pores where the catalyst is entrapped and the oxidative dehydrogenation takes place, and then extracts the products.

According to the invention, the selection of the material precursors and of the sol-gel polycondensation conditions is crucial to obtain efficient oxidation catalysts and to explain the structure-activity relationship deemed of general validity for future heterogeneously catalyzed oxidations capable of meeting the standards required by the new sustainable (or Green) chemistry.

DETAILED DESCRIPTION OF THE INVENTION

Hence, the present invention refers to the preparation and to the use of silica oxides organically modified (ormosils) and doped with tetra-n-propylammonium perruthenate (TPAP) as recyclable selective catalysts of aerobic oxidations of activated and non-activated alcohols, in supercritical carbon dioxide as reaction medium with oxygen as the sole oxidant employed, and this requiring no cosolvent whatsoever in the reaction.

During the catalytic oxidation according to the invention the temperature of the supercritical carbon dioxide is kept within a range of from about 50° to 120° C. at a pressure ranging from about 70 to 240 bar, whereas the partial pressure of the oxygen is kept at a few bars, and in particular in the neighborhood of 1 bar.

In the prior art some different doped ormosils have been synthesized by direct encapsulation of TPAP by means of the sol-gel process, i.e., by hydrolysis and co-polycondensation of $Si(OCH_3)_4$ (TMOS) with different silica trialkoxides bearing different alkyl groups, according to the scheme:

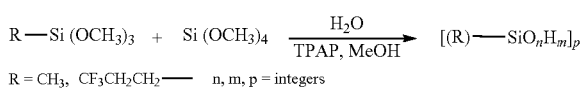

$R = CH_3, CF_3CH_2CH_2—$ n, m, p = integers

The scheme is reported merely by way of example, in no way limitative of the many viable modifications provided by the employment of different precursors or by the use of different reaction conditions. Utilizing the sol-gel methodology, reactive doped materials can easily be prepared under mild conditions as described in (D. Avnir, *Acc. Chem. Res.* 1995, 28, 328) by suitably selecting their own reactivity and their own structural properties (cages hydrophobicity, porosity, surface area, morphology, etc.) to meet casewise the requirements of the chemical conversion merely by varying the preparation conditions (alkoxides, catalyst, pH, metal/water ratio, additives, precursors, cosolvents, drying temperature, etc.) as described in D. Avnir, J. Blum, O. Lev in *The Encyclopedia of Materials: Science and Technology*, (Eds. K. H. J. Buschow, M. C. Flemings, E. J. Kramer, R. W. Cahn, B. Ilschner, S. Mahajan), Elsevier, Amsterdam, 2001; pp. 8040-8049, and references cited therein.

Example 1

According to the invention, a batch (C3-F) of materials was prepared, varying the amount of trifluoropropyl derivative silane monomer and the fluoroalkylsilane:TMOS ratio in the sol-gel co-polycondensation, employing a stoichiometric amount of water ($Si:H_2O=1:4$) and an elevated amount of cosolvent ($Si:MeOH=1:8$).

TABLE 1

Composition of the sol-gel entrapped TPAP catalytic fluoro-ormosils

| Catalyst | TMOS (%) | R-TMS (%)[a] |
|---|---|---|
| C3F-10 | 90 | 10 |
| C3F-25 | 75 | 25 |
| C3F-50 | 50 | 50 |

[a]R = 3,3,3-trifluoropropyl-trimethoxysilane in gels denoted by C3-F and R = 3,3,4,4,5,5,6,6,7,7,8,8,8-tridecaoctafluoro-triethoxysilane in samples with C8-F.

Figure 1:
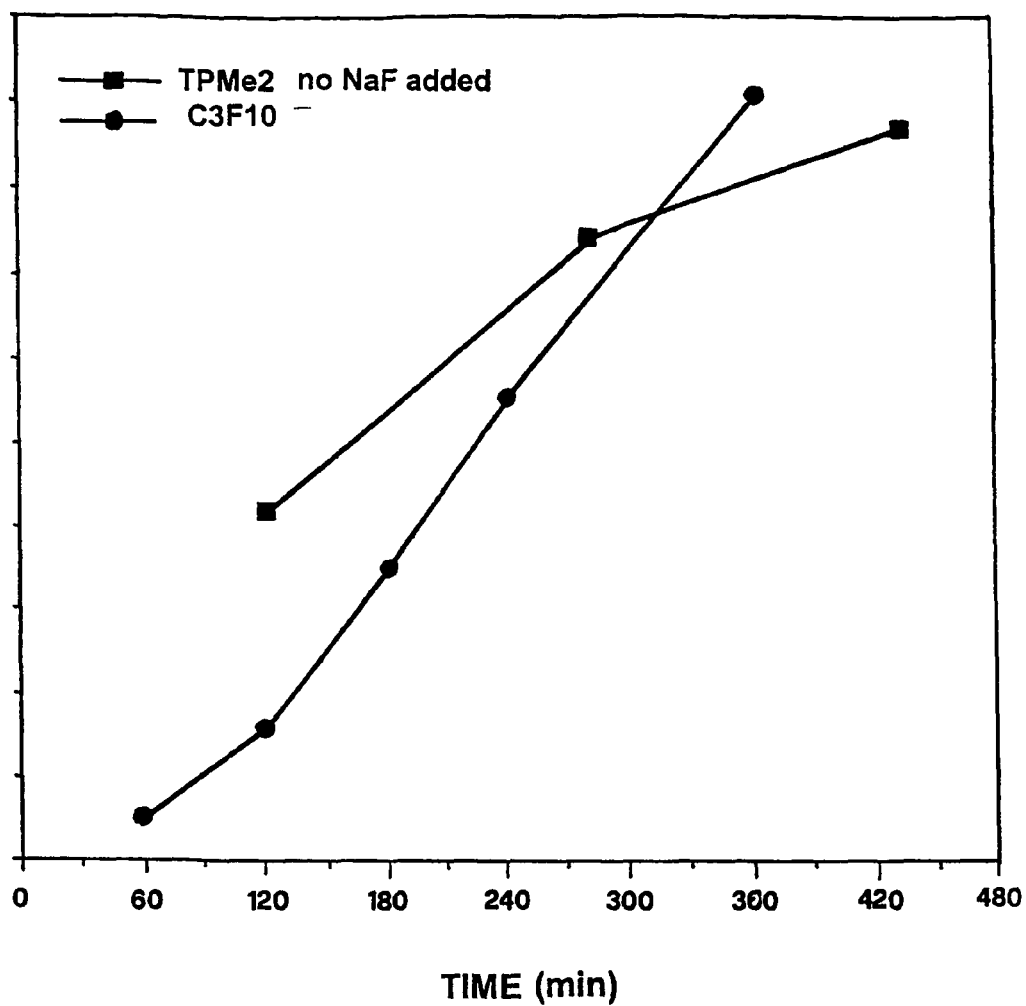
FIG. 1 compares the oxidation rate of TPAP trapped in C3-F-10 10% propyl-fluorinated silicon oxide matrices and 50% methylated TPAP-Me2.

Taking benzyl alcohol as model substrate under the supercritical conditions of scheme 3, the comparison between the reactivity of the TPAP encapsulated in the (most active) 10%-fluoropropyl modified sol-gel C3-F-10 and in 50% methylated gel TPAP-Me-2, shows that a moderate fluorination of the $SiO_2$ matrix affords, under the same reaction conditions, a catalytic activity nearly two times higher ($k_{cat.}$ of $4.5 \times 10^{-3}$ $mol^{-1} min^{-1}$) (See FIG. 1).

With all catalysts the reaction proceeds to completion, no overoxidation of benzyl alcohol to benzoic alcohol being observed, whereas the oxidative dehydrogenation proceeds within the sol-gel cages, as the ruthenium is by no means washed away from the catalyst during the reaction (assessed in reaction samples withdrawn from the sc phase, with a Ru detection limit of <1 ppb). In fact, upon each reaction run the catalyst appears clean and macroscopically unmodified and no post-reaction treatment was necessary to ensure retention of their activity.

The results of Table 2 show that, contrarily to intuition, fluorination per se does not enhance silica-gel reactivity.

TABLE 2

Activity[a] and textural properties of TPAP-doped sol-gel ormosils

| number | catalyst | $K_{cat} \times 10^3$ ($mol^{-1} min^{-1}$) | SSA ($m^2 g^{-1}$) | PSV ($cm^3 g^{-1}$) | Batch ($mmol\ g^{-1}$) |
|---|---|---|---|---|---|
| 1 | C3F-10 | 4.90 | 691 | 0.53 | 0.046 |
| 2 | C3F-25 | 2.14 | 657 | 0.42 | 0.032 |
| 3 | C3F-50 | 2.90 | 458 | 0.31 | 0.027 |

[a]Reaction conditions: 0.048 mmol benzyl alcohol, 10 mol % entrapped TPAP, V = 10 mL, P = 22 MPa, T = 75° C., $O_2$ (1 atm);
* Xerogel obtained using TBAF as condensation catalyst An increase of the fluorination decreases both the surface area and the porosity; whilst the most active catalyst (C3F-10, number 1) has greater pore volume and surface area, surprisingly it also exhibits the lowest fluorination rate (10%); Moreover, a further fluorination up to 25% (C3F-25, number 2) more than halves the catalytic activity, which is only slightly enhanced by an additional fluorination (C3F-50, number 3).

These results suggest a first explanation of the behavior of fluorinated sol-gel oxides in the aerobic oxidation catalysis and provide novel valid information.

The higher reactivity of the short-chain 10%-fluoroalkylated doped gel C3-F-10 is attributable to the negligible viscosity of the supercritical $CO_2$ and to the higher diffusivity of the dissolved molecules of substrate and product through the vast accessible porosity (0.53 $cm^3\ g^{-1}$) of the gel, that accelerates the transfer of molecules to and fro the internal catalyst surface.

The partial burying of the pair of ions of the hydrophobic TPAP in the bulk of the resulting silica oxide xerogel, making them inaccessible for catalysis, is prevented by the elevated amount of methanol used in the synthesis of the sol-gel materials. Methanol destroys the micellar aggregates, typical of the first stages of the sol-gel process, in which the slowly generated R—Si(OH)$_3$ monomers tend to arrange with the polar —Si(OH)$_3$ groups at the forefront of the growing sol-gel material, and the hydrophobic nonpolymerizable R residue orientating away from the interfacial strongly hydrogen-bonding solvent (water/methanol).

Without being bound to this hypothesis, thus the higher reactivities of the catalysts of batch C3-F with a lesser fluorination are explained. In fact, in this case the shorter fluoroalkyl chain favors the hydrolysis and slows down the condensation, so that rapid aggregation of the early sol particles is prevented and TFPTMOS can fully hydrolyze to $CF_3CH_2CH_2$—Si(OH)$_3$ and this co-polymerize with the Si(OH)$_4$ monomers obtained by the parallel (and faster) hydrolysis of TMOS. A porous open network is formed in which most of the TPAP molecules dissolved in the original gel are encapsulated at the surface of the resulting silica oxide cages, where they are accessible for catalysis.

On the other hand, the cages are massively fluorinated, despite the low fluoroalkyl:TMOS ratio, as the terminal fluoroalkyl groups concentrate mostly at the surface of the cages, favoring the diffusion of the fluorophilic $CO_2$. The predominant role of the textural properties in controlling the reactivity of the materials under compressed carbon dioxide is coherent with the appreciable reactivity observed with TPAP encapsulated in unmodified $SiO_2$; TPAP is virtually inactive in toluol, and it exhibits a marked catalytic activity in $scCO_2$, as described in (M. Pagliaro, R. Ciriminna, *Tetrahedron Lett.* 2001, 42, 4511). The pore size distribution obtained by $N_2$ adsorption clearly reveals that the C3F-10 is a microporous glass with a type I adsorption isotherm.

As doped sol-gels the materials are highly versatile, and, e.g., analogous commercial doped ormosils have already attained a "second-generation" performance level, being easily suitable for heterogeneous continuous oxidations in dense-phase carbon dioxide with important practical advantages.

Hence, considering their importance, both commercial and for the production of selective catalytic oxidations of alcohols, and the fact that heterogeneous sol-gel catalysts according to the invention can easily be adapted to continuous conversions in compressed $CO_2$, their yield mainly depending on the temperature and on the reactants concentration, which may independently be controlled to optimize the conditions, it will be understood that the present invention is of primary industrial importance.

Example 2

Catalysts Preparation

Several fluorinated xerogels were prepared by processing according to the sol-gel methodology a monomer containing fluoroalkyls (3,3,3-trifluoropropyl-trimetoxysilane, TFPTMOS purchased from Fluka; or 3,3,4,4,5,5,6,6,7,7,8,8,8-tridecaoctafluoro-triethoxysilane, TDOFTEOS purchased from ABCR, Karlsruhe) with tetramethylorthosilicate (TMOS) in the presence of TPAP dissolved in methanol, and keeping constant the Si:MeOH:H$_2$O molar ratio at 1:8:4. Other chemical products comprising benzyl alcohol, n-decane, TMOS and TPAP were purchased from Sigma Aldrich and used without further purification. Ultra pure water (Millipore Type 1) was used in all the preparations.

A. Typical Fluorinated "Sol-Gel" Catalysts Preparation Procedures.

Batch C3-F. A typical silica gel C3-F-10 doped with 10% fluoropropyl was synthesized by adding TMOS (2.68 mL) and TFPTMOS (0.39 mL) to a solution of TPAP (24.5 mg) in MeOH (6.45 mL) cooled in an ice bath, followed by the addition of H$_2$O (1.44 mL). The mixture was stirred for 30 min, then it gelled yielding a black alcogel that was sealed and left to age at room temperature for 24 h prior to drying at 50° C. (5 days). The grey xerogel thus obtained was powdered, washed under reflux (CH$_2$Cl$_2$×2, 40° C.) and dried at 50° C. prior to use.

Batch C8-F. A typical silica gel C8-F-25 doped with 25% perfluorooctyl was synthesized as reported above, by mixing TMOS (2.63 mL) and TDOFTEOS (1.12 mL) along with a solution of TPAP (21.3 mg) in MeOH (5.67 mL), and subsequent addition of H$_2$O (1.42 mL). The resulting alcogel was treated as described above for C3-F-25, yielding a grey powder with a typical catalytic load of 0.022 mmol/g.

Analysis and Reaction Rate.

The carbonyl products content was determined by GC analysis on a Shimadzu chromatograph equipped with a Supelcowax 10 capillary column (30 m, 0.25 mm ID) using the internal standard method (with previously calculated response factors). The constant rates $k_{cat.}$ were determined from the aldehyde formed by integrating the pseudopoints of the first order obtained from a quadratic equation in which a reactant ($O_2$ in this case) is in great excess, i.e., $\ln(1-[ald.]_t/[ald.]_{t=\infty})=-k_{cat}[O_2]t$. The $N_2$-BET textural values were obtained with a Carlo Erba Instruments Sorptomatic 1900 powder analyzer, and the Ru content assessed by ICP-MS on a HP 4500 spectrometer.

B. Typical Alcohol Oxidation Procedure.

The reaction conditions were chosen so as to ensure complete solubility of the alcohol and of the aldehyde (Scheme 3) in the homogeneous supercritical phase, and a typical oxidation was carried out in the modified Carlo Erba SFC 3000 reactor described in (S. Campestrini, U. Tonellato, Adv. Synth. Catal. 2001, 343, 819) at 75° C. and 22 Mpa, where the $scCO_2$ exhibits a density of 0.67 g/mL. Benzyl alcohol (5 µL, 0.5 mmol) and 0.1 equiv. of catalyst C3-F-25 (156 mg) along with n-decane (5 µL, 1 mmol) as internal standard were added to the reaction vessel. Then, after flowing the oxygen (1 bar), the reaction vessel was sealed and placed into a thermostated oven. Liquid $CO_2$ was then pumped into the autoclave using a cryogenic pump to bring the reactor pressure at 22 MPa. The reaction mixture was kept under stirring at 400 rpm (by means of an alternating magnetic field stirrer) at the set temperature for the desired reaction time. Reaction samples were withdrawn through a 6-way valve connected to a restrictor (kept at 90° C.) and trapped in dichloromethane prior to GC analysis. When the reaction was complete, the heating was stopped and the system allowed to cool to room temperature. The reactor was thus opened and the $CO_2$ gradually vented off in $CH_2Cl_2$, letting the total pressure inside the reactor reach the atmospheric value. Then, the product was extracted with a further amount of $CH_2Cl_2$ and the recovered catalyst was dried and reused as such in a subsequent reaction run.

Example 3

Sol-Gel Catalysts Preparation

On the basis of the third aspect of the invention, and of the Applicant's research, several catalytic ormosils were synthesized by sol-gel hydrolysis and co-polycondensation of RTMS (alkyltrimetoxysilane) and TMOS (tetramethoxyorthosilicate) in the presence of TPAP dissolved in methanol with and without NaF as polycondensation catalyst, varying the parameters consisting of the (Si:MeOH:$H_2O$) proportion, the organosilane/siloxane (RTMS/TMOS) Si ratio, the amount of MeOH cosolvent and the amount of $H_2O$, (batch A, Si:MeOH:$H_2O$=1:8:1; batch B, Si:MeOH:$H_2O$=1:4:4).

Among RMTS silanes, methyltrimethoxysilane (MTMS), ethyltrimethoxysilane (ETMS) and propyltrimethoxysilane (PTMS) and the like were used.

Among siloxanes, besides TMOS, tetraethoxyorthosilicate and the like may be mentioned.

Reference has hereto been made to methanol as cosolvent, however, it is evident that other cosolvents may be selected without departing from the scope of the present invention.

In Table 3 the ormosils produced according to the present invention are shown, divided into two batches (Batch A and Batch B) with their identifying acronyms. These materials differ thereamong owing to the different ratio thereof for the parameters indicated above.

TABLE 3

Composition of the sol-gel entrapped TPAP A and B catalytic ormosils.
Batch A: Si:$H_2O$:MeOH = 1:8:1
Batch B: Si:$H_2O$:MeOH = 1:4:4

| Batch A | Batch B | TMOS (%) | MTMS (%) | ETMS (%) | PTMS (%) |
|---|---|---|---|---|---|
| A-Me0 | B-Me0 | 100 | 0 | — | — |
| A-Me1 | B-Me1 | 75 | 25 | — | — |
| A-Me2 | B-Me2 | 50 | 50 | — | — |
| A-Me3 | B-Me3 | 25 | 75 | — | — |
| A-Me4-F[a] | B-Me4-F[a] | 0 | 100 | — | — |
| A-Et2-F[a] | B-Et2-F[a] | 50 | — | 50 | — |
| A-Pr2-F[a] | B-Pr2-F[a] | 50 | — | — | 50 |

[a]Gels obtainable only by using NaF as gelation catalyst. All other gels were obtained with and without NaF.

Example 4

Preparation of a Typical Catalyst of Batch A

A typical catalyst of batch A, obtained with NaF denominated A-Me3, is prepared by adding MTMS (1.65 mL) and TMOS (5.90 mL) to a solution of TPAP (55.5 mg) in MeOH (1.80 mL) cooled in an ice bath (to prevent formation of flames) followed by the addition of $H_2O$ (5.70 mL) and NaF (765 µL, 1 M) under fast stirring. The sol gels rapidly and the resulting alcogel is sealed and left to age at room temperature for 48 h prior to drying in an oven at 50° C. until reaching constant weight (5 days). The catalytic dry gel (xerogel) thus obtained is powdered, washed under reflux ($CH_2Cl_2\times2$, 60° C.) and dried at 50° C. prior to use.

Example 5

Preparation of a Typical Catalyst of Batch B

A typical catalyst of batch B is prepared by adding MTMS (4.90 mL) and TMOS (1.95 mL) to a solution of TPAP (55.5 mg) in MeOH (7.30 mL) cooled in an ice bath followed by the addition of $H_2O$ (2.65 mL) under fast stirring. The sol gels slowly and the alcogel thereby obtained is sealed and left to age at room temperature for 48 h prior to drying in an oven at 50° C. until reaching constant weight (5 days). The resulting xerogel is washed as reported above. A typical catalytic load is 500 mmol TPAP/g ormosil.

Example 6

Oxidation Procedure

Catalytic Activity in Toluene.

A solution of cinnamyl alcohol (26.2 µL, 0.5 mmol) in toluene (4 mL) kept at 75° C. in an oil bath is additioned with n-decane (26.2 µL, internal standard) and 430 mg (0.1 equiv.) of the sol-gel encapsulated catalyst A-Me3. Then, oxygen is flown for some minutes and the reaction mixture kept under a pure oxygen atmosphere ($O_2$ balloon method) and under fast stirring by means of a magnetic stirrer. The reaction is followed at GC; when the reaction is complete, the catalyst is filtered (Whatman filter paper, grade 1), washed under reflux with $CH_2Cl_2$, dried at 50° C. and used as such in a subsequent reaction run. Small losses of material are taken into account, equivalently decreasing the substrate so as to keep constant the catalyst:substrate ratio at 10 mol %.

Results and Comments

Figure 2:
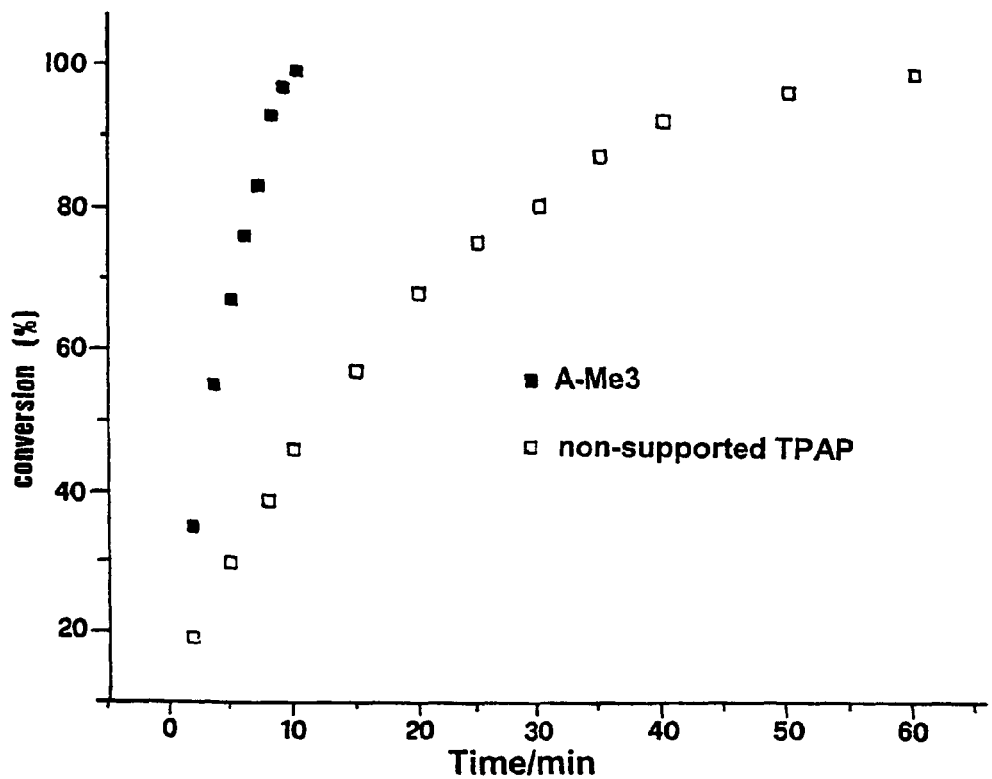
FIG. 2 compares the reactivity of TPAP unsupported and TPAP encapsulated in the silica matrix A-Me3.

Surprisingly, with reference to FIG. 2 of the annexed drawing, the comparison between the reactivity of TPAP unsupported and encapsulated in the silica matrix A-Me3 (75% methylated) in the toluene/oxygen oxidation protocol of benzyl alcohol shows that sol-gel encapsulation of the TPAP within a hydrophobic silica matrix enhances its activity, with the reaction going to completion at a much faster rate (about 6 times faster) than under homogeneous conditions.

Figure 3:
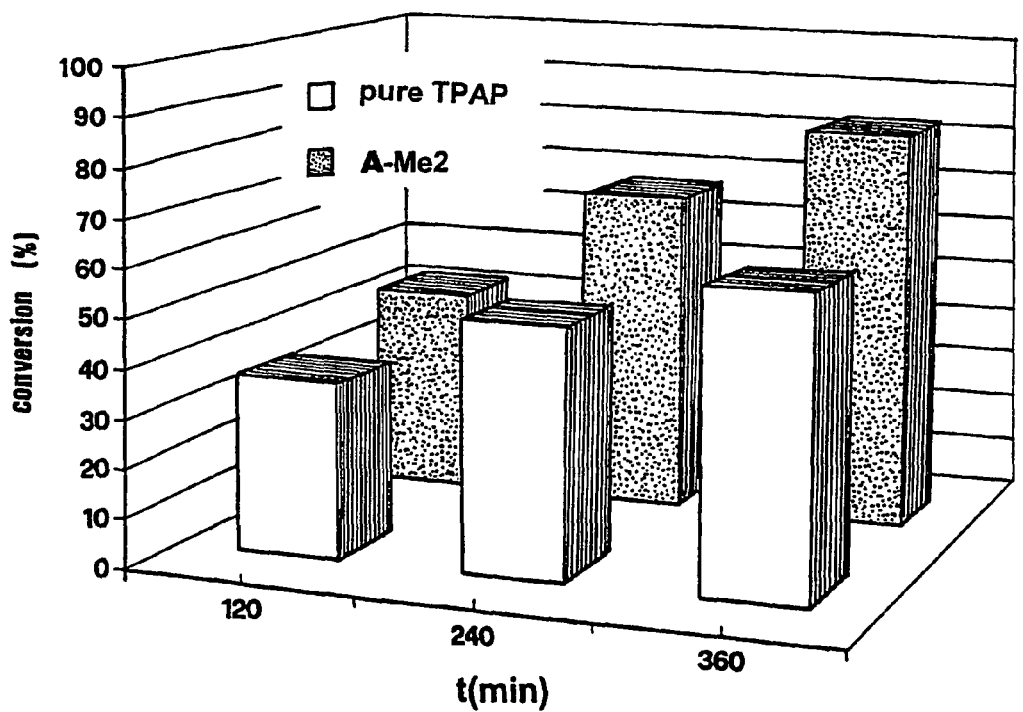
FIG. 3 compares the reactivity of TPAP unsupported and TPAP encapsulated in a sol-gel ormosil A-Me2.

This result was accurately investigated, and the oxidation repeated with the same catalytic amount of free TPAP (10 mol %) with and without 4 Å-molecular sieves. However, no significant change is observed and under the applied reaction conditions the activity of the sol-gel encapsulated catalyst A-Me3 remains much higher than that of dissolved TPAP (FIG. 3).

Moreover, interestingly up to a 40-50% conversion that is typical of TPAP-mediated aerobic oxidations of alcohols the heterogeneous kinetic curve does not exhibit the slow stage (which is probably due to the formation of $RuO_2$, which confined within a zeolite matrix becomes an improved aerobic oxidant of alcohols) subsequent to the fast stage, thereby showing that the reaction mechanism may not necessarily be the same when oxidative dehydrogenation takes place within sol-gel nanocavities.

In fact, in all tested cases, the reaction mediated by the catalytic gels at issue is heterogeneous in nature, as is proved by the fact that no further reactivity of the "hot" reaction filtrate is observed following the rapid filtration of the catalyst shortly after the onset of the reaction (at about the 50% of alcohol conversion). Likewise, other non-reactive Ruthenium species are not leached by the solid catalyst during the reaction, since neither the 'hot' filtrate nor the reaction samples withdrawn from the liquid phase during catalysis exhibit any amount of Ruthenium (ICP-MS, sensitivity <1 ppb).

Analogous results are obtainable by using dichloromethane as solvent.

Example 7

Oxidation Procedure in $scCO_2$

Catalytic Activity in Supercritical Carbon Dioxide.

Benzyl alcohol (5 μL, 0.5 mmol) and 0.1 equiv. of catalyst A-Me1 (100 mg) are added along with n-decane (5 μL, 1 mmol) as internal standard to the reaction vessel and the reaction conditions chosen to ensure complete solubility of the alcohol and of the benzyl aldehyde (Scheme 2) in the homogeneous supercritical phase. In order to do so, 0.5 mmol of substrate and 0.5 mmol of product are dissolved along with the internal standard in 10 mL $CH_2Cl_2$ analyzing its content at GC (gas chromatograph), prior to charging the reactor with the same amounts of substrate, product and internal standard. Keeping constant the reaction vessel temperature at 75° C., the $CO_2$ pressure inside the reactor is varied from 140 to 240 bar analyzing the content at GC in order to check the substrate and product dissolution (for comparison with the dichloromethane solution) which is complete at 220 bar.

Hence, after having been charged with oxygen at room temperature (1 bar partial pressure), the reactor is sealed and placed into an oven thermostated at 75° C. Liquid $CO_2$ is then pumped into the autoclave using a cryogenic pump to bring the pressure inside the reactor to 220 bar while the reaction mixture is kept under stirring at 400 rpm (by means of an alternating magnetic field stirrer) at the set temperature for the desired reaction time. Samples withdrawn through the stainless steel restrictor (kept at 90° C. to prevent any condensation) are trapped in dichloromethane prior to GC analysis; when the reaction is complete, the heating is stopped and the system allowed to cool to room temperature. The reactor is thus opened and the gaseous $CO_2$ gradually vented off in $CH_2Cl_2$. When the total pressure inside the reactor reaches the atmospheric value, the product is extracted with a further aliquot of $CH_2Cl_2$ and the catalyst is recovered, dried and used as such in a subsequent reaction run.

Results and Comments.

With reference to FIG. 3 of the annexed drawing, in this case as well the comparison between the reactivity of TPAP unsupported and encapsulated in the sol-gel ormosil A-Me2 (50% methylated) in the aerobic oxidation of benzyl alcohol in supercritical carbon dioxide under the conditions of Scheme 2, shows immediately that sol-gel encapsulation of the TPAP enhances its activity.

Interestingly, it may be noted that despite the insolubility of the ionic species $(Pr)_4N$—$RuO_4$ in supercritical $CO_2$ phase, a moderate degree of activity is observed with reaction going to completion in 11 hours. Again, the reaction mediated by gel A-Me2 takes place within the sol-gel cavities of the material and is heterogeneous in nature since no ruthenium is detected in reaction samples withdrawn during reaction from the supercritical phase (with a Ru detection limit <1 ppb).

Technical Progress and Inventive Activity.

The technological advantages of the catalysts and of the oxidation process in supercritical $CO_2$ according to the invention are at least four, as disclosed hereinafter.

a). Stability and Recyclability.

With respect to other well-known resins, silica gels generally provide various advantages, being independent of the solvent used (rigid porous structure and no swelling), incapable of non-specific bonding (high yields) and capable of a very high catalytic load (small volume of gel required).

With all substrates, the catalytic sol-gels according to the invention proved leach-proof and recyclable, requiring only a step of washing under reflux with $CH_2Cl_2$ between subsequent reaction runs. The valuable ruthenium TPAP compound, impossible to recycle under homogeneous conditions and slowly forming a black precipitate in the form of sol, owing to the encapsulation in a hydrophobic silica matrix, is instead physically and chemically stabilized and may be recycled without losses of valuable ruthenium. E.g., comparison between the intermediate yields observed with a typical hydrophobic silica matrix (A-Me3) in subsequent reaction runs (which truly measures a catalyst stability), clearly shows that aside from a minor loss after the first reaction run (about 5%, probably due to formation of $RuO_2$), catalyst reactivity, which in case of absolute stability should keep constant, remains practically unvaried.

The known stability towards leaching of onium ion pairs physically encapsulated in sol-gel matrices is thus confirmed also for TPAP, whose filtration is rapidly carried out at the reaction temperature in order to prevent any possible perruthenate readsorption by the solid matrix. Hence, as mentioned above, the reaction filtrate obtained from the hot filtering of the 50%-converted catalyst heated to 75° C. under $O_2$, gives no further oxidation of the residual substrate, even after 12 h.

The abovedisclosed result evidently stands out from the prior art, in which the full leaching of the $RuO_4^-$ physically supported in the mesoporous cavities of silica zeolite MCM-41 was had in a single reaction run; i.e., instability and impossibility of recycling the perruthenate chemically supported on polystyrene resin (PSP).

b). Selectivity.

Sol-gel encapsulation in hydrophobic matrices determines the full conservation of the capability of selectivity of homogeneous-phase TPAP, as it is shown by a test of the selectivity of the material for primary hydroxyls compared to secondary hydroxyls. This is an important property of perruthenate-mediated oxidations.

In fact, as it is shown in Table 4, row 1, by carrying out in one-pot the oxidation of a 1:1 benzyl alcohol:1-phenylethanol with the same hydrophobic gel A-Me3, after 10 min all the primary benzyl alcohol is already converted, as compared to the 19% of 1-phenylethanol dehydrogenated to acetophenone.

However, in marked contrast with respect to the perruthenate heterogeneized on polystyrene resin (PSP) of the prior art, all the secondary alcohol left in solution can be further oxidized simply by prolonging the reaction time. This proves the potentiality that these materials possess for combinatorial applications, where such a selectivity and versatility are in great demand. As illustrated in Table 4, row 4, the full keeping of the selective capability of TPAP in a solution is proved by the lack of oxidation of the olefinic double bonds in the oxidation of trans-cinnamyl alcohol that, in the presence of the 10 mol % TPAP encapsulated in gel A-Me3, is rapidly (2 h) converted in high yields (99%) to trans-cinnammaldehyde.

TABLE 4

Aerobic oxidation of alcohols mediated by catalyst based on TPAP encapsulated in A-Me3[a]

| row | substrate | product | conv (%) | time |
|---|---|---|---|---|
| 1 | benzyl alcohol | benzaldehyde | 96 | 10 min |
|   | 1-phenylethanol | acetophenone | 98 | 3 h |
| 2 | cyclohexanol | cycloexanone | 45 | 6 h |
| 3 | 1-octanol | octylaldehyde | 96 | 5 h |
| 4 | trans-cinnamyl alcohol | trans-cinnamaldehyde | 99 | 2 h |

[a]Reaction conditions: 0.2 mmol substrate, 10 mol % encapsulated TPAP, 4 mL solvent, T = 75° C., $O_2$ (1 atm).

c). Versatility

The generality of the method is proved by the fact that the same catalytic ormosil A-Me3 operates in the conversion of the less readily oxidizable aliphatic and allylic alcohol substrates (See Table 4).

In fact, cyclohexanol (row 2, Table 4) which cannot be oxidized by TPAP encapsulated within mesoporous cavities of the silica zeolite MCM-41 of the prior art, in this case is rapidly converted with hydrophobic silica A-Me3 yielding a cyclohexanone conversion of 45% after 6 h and a final conversion of 58%, which is the same observed when the reaction is carried out with homogeneous-phase TPAP.

Moreover, this excellent activity due to the sol-gel encapsulation of the TPAP in hydrophobic matrices, is not limited to cyclic substrates, as shown by the rapid oxidation in high yields of the aliphatic substrate 1-octanol (row 3, Table 4) giving, over a mere 5 h, a 96% yield of octyl aldehyde, proving the significant versatility of these catalysts.

d). Sustainability and Applicability to Continuous Processes.

The high yields in supercritical phase of the hydrophobic sol-gel matrices according to the invention make the alcohol oxidation process sustainable, as they allow to eliminate both the heavy metals traditionally used as stoichiometric oxidants and the volatile organic solvents from the conversion process, whereas the catalysts can easily be adapted to continuous oxidizing processes in supercritical phase, giving specific economic, technical, environmental and safety advantages.

In fact, thanks to the high compressibility, the lack of flammability and the solvent power of $CO_2$ in supercritical phase, catalytic reactions on solid catalysts are carried out on an industrial scale in small reactors, blowing in the reactants and separating (and recycling) the $CO_2$ from the products by a mere pressure release. On the other hand, the doped sol-gel materials, thanks to their unprecedented chemical and physical versatility, can easily be prepared in the form of membranes of desired shape, and optionally further stabilized on solid matrices like SIRAN sintered glasses or Celite.

Thus, the solid catalysts for oxidation according to the invention meet all the industrial requirements of high activity, selectivity, stability and chemical and physical versatility.

The invention claimed is:

1. A sol-gel process for the production of nanohybrid sol-gel materials for heterogeneous aerobic catalysis containing tetra-n-propylammonium perruthenate (TPAP) entrapped in a sol-gel matrix, comprising hydrolyzing and co-polymerizing organosilanes and silanes in the presence of said TPAP, water, and an organic cosolvent; wherein said co-polymerization is carried out with a precursor fluorinated organosilane amount of up to 25 mol % of the co-polymerization mixture and a non-fluorinated silane monomer; and wherein the molar ratio among the total silica (Si), as fluorinated organosilane+silane, the amount of cosolvent, and the amount of water is in the range from 1:4:4 to 1:8:8.

2. The process according to claim 1, wherein said fluorinated organosilane and said silane are in the form of metal alkoxides.

3. The process according to claim 2, wherein said precursor fluorinated organosilane is a fluorinated silicon alkoxide.

4. The process according to claim 3, wherein said fluorinated silicon alkoxide is a compound of the formula $n$R—Si(OCH$_3$)$_3$ wherein n is 1, and R represents F or a fluorinated alkyl chain selected from the group consisting of $CF_3(CH_2)_2$, $CF_3(CF_2)_7CH_2CH_2$, and $CF_3(CF_2)_5CH_2CH_2$.

5. The process according to claim 3, wherein said fluorinated organosilanes have the formula RR'Si(OCH$_3$)$_2$; R represents F— or a fluorinated alkyl chain selected from the group consisting of $CF_3(CH_2)_2$—, $CF_3(CF_2)_7CH_2CH_2$—, and $CF_3(CF_2)_5CH_2CH_2$—; and R' is a non-hydrolyzable substituent organic group.

6. The process according to claim 5, wherein said non-hydrolyzable substituent organic group is $CH_3$—, $CH_3CH_2$—, or $CH_3CH_2CH_2$—.

7. The process according to claim 1, wherein said non-fluorinated silane monomer is Si(OCH$_3$)$_4$ (TMOS), Si(OCH$_2$CH$_3$)$_4$ (TEOS), or a mixture thereof.

8. The process according to claim 1, wherein said cosolvent is methanol, ethanol, propanol, or a combination thereof.

9. The process according to claim 1, wherein the cosolvent is (MeOH), and the molar ratio Si:MeOH:H$_2$O is 1:8:4.

10. A process for the selective heterogeneous aerobic catalytic oxidation of alcohols to carbonyls in a solvent, comprising employing as catalyst a nanohybrid sol-gel material based on silica organically modified and doped with the ruthenium species tetra-n-propylammonium perruthenate (TPAP), produced via a process according to claim 1, and employing a solvent selected from the group consisting of toluene, dichloromethane, and supercritical carbon dioxide.

11. The process according to claim 10, wherein oxygen at atmospheric pressure is employed as primary oxidant.

12. The process according to claim 10, wherein during the catalytic oxidation the temperature of the supercritical carbon dioxide is kept within a range of from 50° C. to 120° C. at a pressure of from 70 bar to 240 bar, and the partial pressure of the oxygen is kept at about 1 bar.

13. The process according to claim 10, wherein benzyl alcohol, 1-phenylethanol, cyclohexanol, 1-octanol, or trans-cinnamyl alcohol is oxidized.

14. Nanohybrid sol-gel catalyst for the heterogeneous aerobic catalysis containing tetra-n-propylammonium perruthenate (TPAP) entrapped in the sol-gel matrix obtained by a process as claimed in claim 1.

15. Nanohybrid sol-gel catalyst for the heterogeneous aerobic catalysis containing tetra-n-propylammonium perruthenate (TPAP) entrapped in the sol-gel matrix obtained by a process as claimed in claim 4.

16. Nanohybrid sol-gel catalyst for the heterogeneous aerobic catalysis containing tetra-n-propylammonium perruthenate (TPAP) entrapped in the sol-gel matrix obtained by a process as claimed in claim 5.

17. Nanohybrid sol-gel catalyst for the heterogeneous aerobic catalysis containing tetra-n-propylammonium perruthenate (TPAP) entrapped in the sol-gel matrix obtained by a process as claimed in claim 9.

18. The process according to claim 1, wherein said cosolvent comprises methanol.

19. A sol-gel process for the production of nanohybrid sol-gel materials for heterogeneous aerobic catalysis containing tetra-n-propylammonium perruthenate (TPAP) entrapped in a sol-gel matrix, comprising hydrolyzing and co-polymerizing organosilanes and silanes in the presence of said TPAP, water, and an organic cosolvent; wherein said co-polymerization is carried out with a precursor fluorinated organosilane amount in the range from 10 mol % to 25 mol % of the co-polymerization mixture and a non-fluorinated silane monomer; wherein the molar ratio among the total silica (Si), as fluorinated organosilane+silane, the amount of cosolvent, and the amount of water is in the range from 1:4:4 to 1:8:8.

20. The process according to claim 19, wherein said cosolvent comprises methanol.

21. A process for the selective heterogeneous aerobic catalytic oxidation of alcohols to carbonyls in a solvent, comprising employing as catalyst a nanohybrid sol-gel material based on silica organically modified and doped with the ruthenium species tetra-n-propylammonium perruthenate (TPAP), produced via a process according to claim 18, and employing a solvent selected from the group consisting of toluene, dichloromethane, and supercritical carbon dioxide.

22. Nanohybrid sol-gel catalyst for the heterogeneous aerobic catalysis containing tetra-n-propylammonium perruthenate (TPAP) entrapped in the sol-gel matrix obtained by a process as claimed in claim 18.

* * * * *